US012245861B1

(12) United States Patent
Jeyanandarajan

(10) Patent No.: US 12,245,861 B1
(45) Date of Patent: Mar. 11, 2025

(54) ELECTRODE HEADGEAR FOR USE IN ELECTROENCEPHALOGRAPHY

(71) Applicant: Qneuro, Inc, Irvine, CA (US)

(72) Inventor: Dhiraj Jeyanandarajan, Irvine, CA (US)

(73) Assignee: Qneuro, Inc, Irvine, CA (US)

( * ) Notice: Subject to any disclaimer, the term of this patent is extended or adjusted under 35 U.S.C. 154(b) by 0 days.

(21) Appl. No.: 18/512,138

(22) Filed: Nov. 17, 2023

(51) Int. Cl.
*A61B 5/256* (2021.01)
*A61B 5/291* (2021.01)
*A61B 5/31* (2021.01)

(52) U.S. Cl.
CPC ............. *A61B 5/256* (2021.01); *A61B 5/291* (2021.01); *A61B 5/31* (2021.01)

(58) Field of Classification Search
CPC ............ A61B 5/256; A61B 5/291; A61B 5/31
See application file for complete search history.

(56) References Cited

U.S. PATENT DOCUMENTS

| | | | | |
|---|---|---|---|---|
| 3,706,308 A | * | 12/1972 | John ...................... | A61B 5/291 600/483 |
| 3,870,965 A | * | 3/1975 | Frederiksen ............ | H03F 1/302 330/288 |
| 4,709,702 A | * | 12/1987 | Sherwin ................ | A61B 5/6803 607/139 |
| 2001/0044573 A1 | * | 11/2001 | Manoli ................. | A61B 5/6804 600/383 |
| 2011/0043225 A1 | * | 2/2011 | Sullivan ................. | A61B 5/302 324/658 |
| 2013/0245480 A1 | * | 9/2013 | Crockford ............. | A61B 5/349 600/509 |
| 2014/0020089 A1 | * | 1/2014 | Perini, II ................. | G07C 9/37 726/19 |
| 2015/0282760 A1 | * | 10/2015 | Badower .............. | A61B 5/6803 600/383 |
| 2015/0343196 A1 | * | 12/2015 | Vasapollo .............. | A61N 1/048 607/45 |
| 2017/0055903 A1 | * | 3/2017 | Cramer ................ | A61B 5/6833 |

* cited by examiner

*Primary Examiner* — Jacqueline Cheng
*Assistant Examiner* — Tho Q Tran
(74) *Attorney, Agent, or Firm* — Sheppard Mullin Richter & Hampton LLP

(57) ABSTRACT

An apparatus comprises a dual electrode assembly comprising: a non-contact electrode, a dry electrode having multiple contact pins, and a housing configured to enclose the dry electrode when the dry electrode is in a first position, and to expose the multiple contact pins outside the housing when the dry electrode is in a second position.

17 Claims, 18 Drawing Sheets

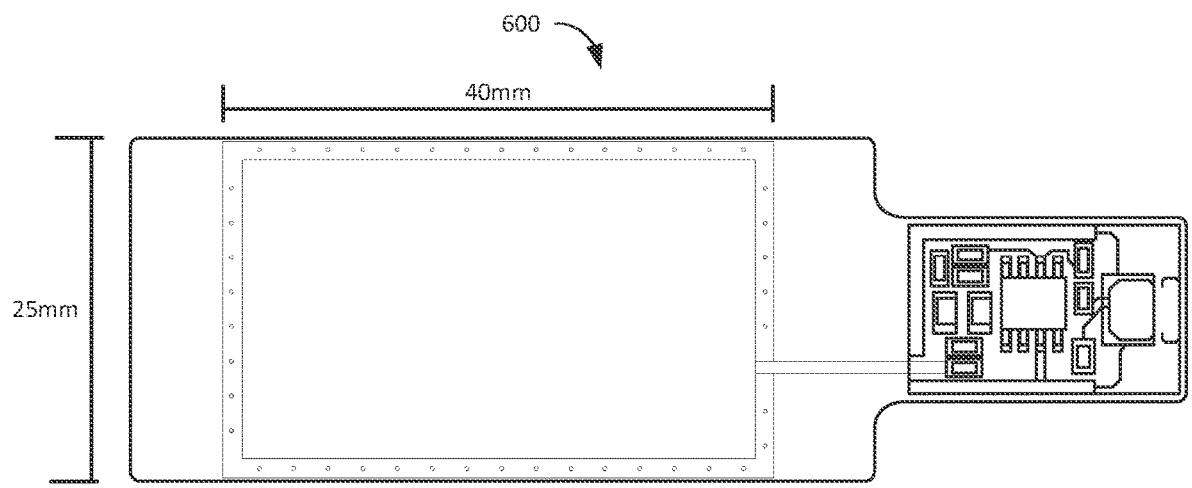
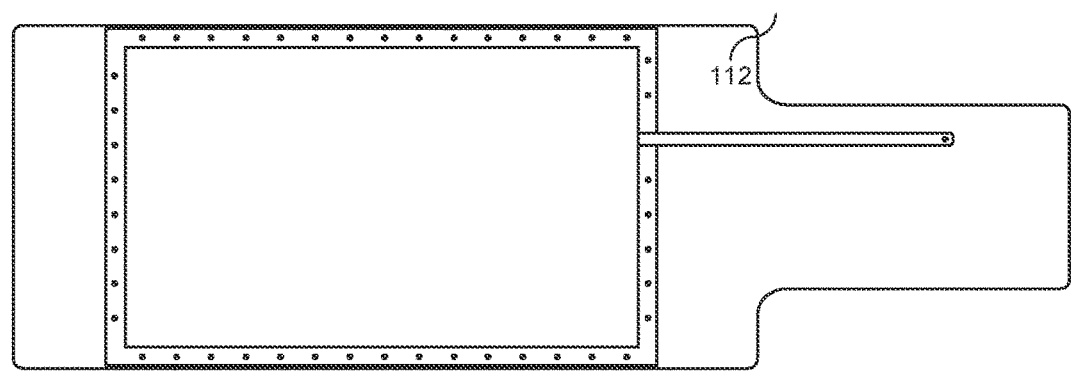
FIG. 6
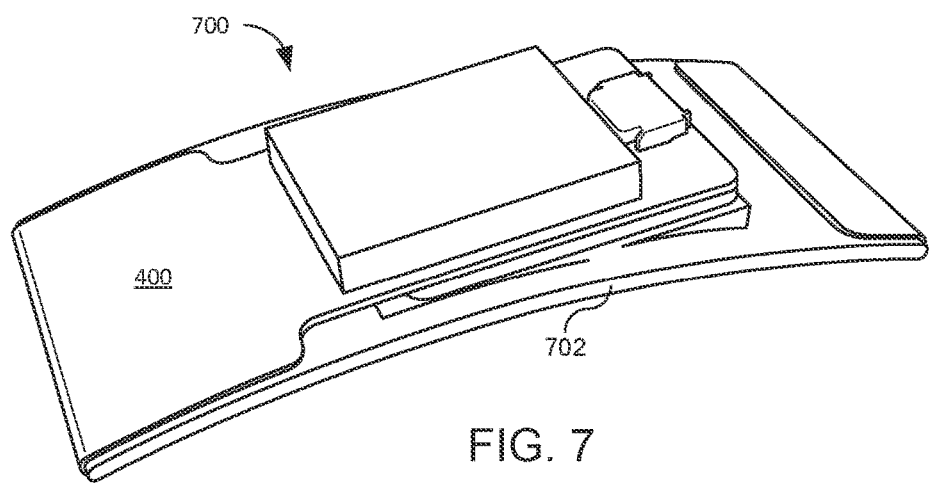
FIG. 7

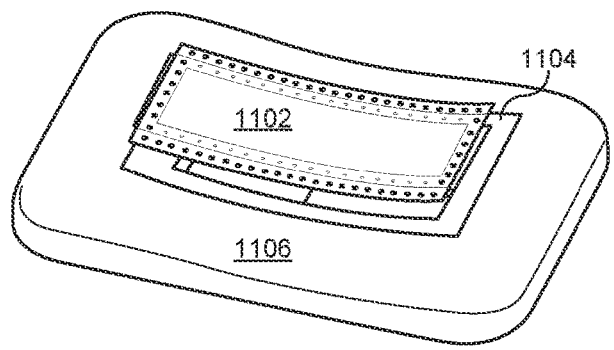
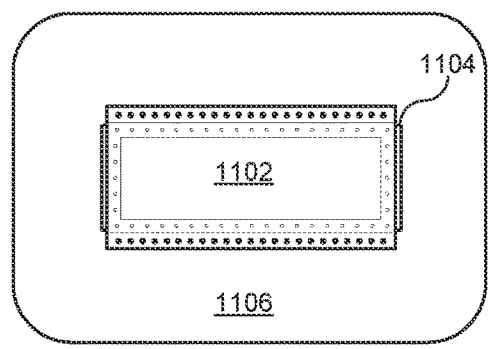
FIG. 11A　　　　　　　　FIG. 11B
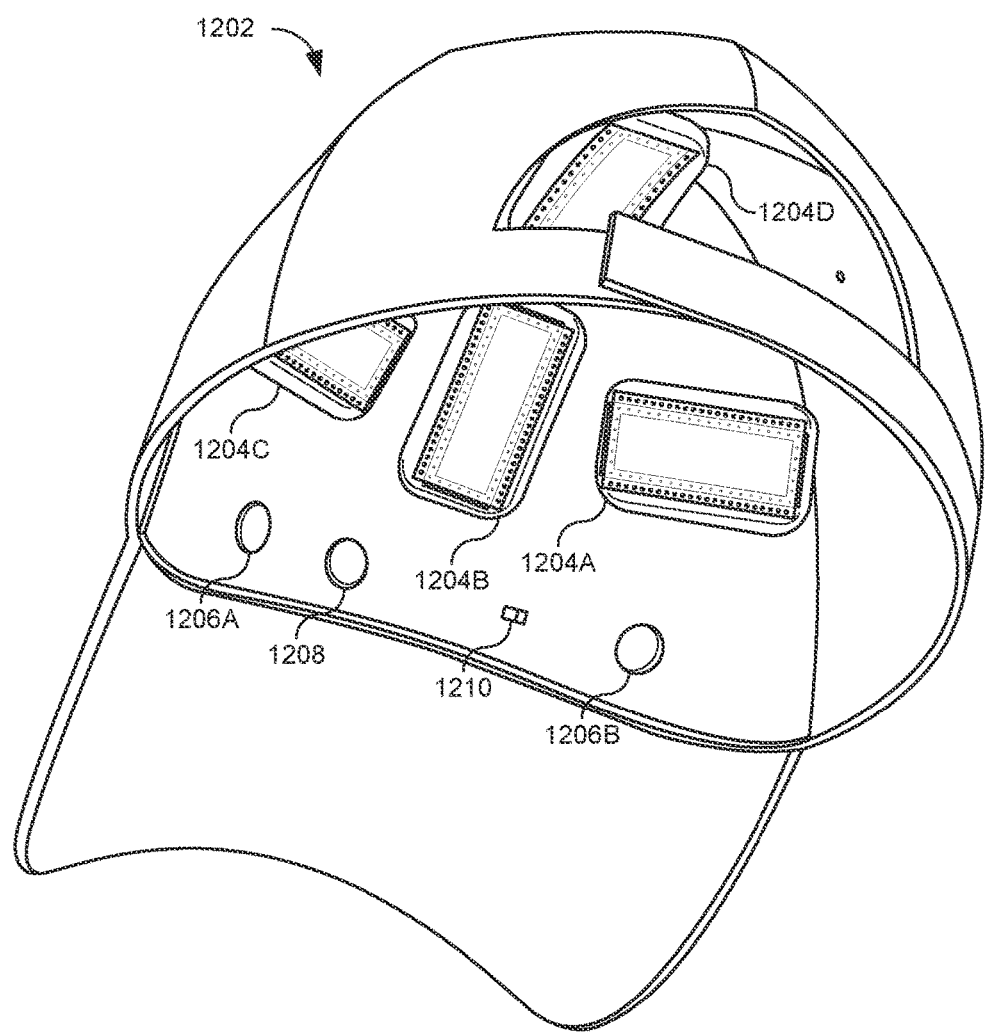
FIG. 12

ELECTRODE HEADGEAR FOR USE IN ELECTROENCEPHALOGRAPHY

DESCRIPTION OF RELATED ART

The disclosed technologies relate generally to headgear comprising electrodes for electroencephalography, and more particularly some embodiments relate to the electrodes.

BACKGROUND

Bio-potential recording techniques such as electroencephalography generally employ Ag/AgCl electrodes with adhesives or gels that couple the electrodes directly to the scalp over the area where electrical potentials are to be recorded. The basic principle of operation of conventional electroencephalography electrodes is well known. When a conventional electroencephalography electrode is placed over the scalp, an electrochemical reaction takes place at the junction of the electrolyte and the metal of the electrode due to electrical transfer by oxidation and reduction reactions. The electrochemical reaction produces electrical signals representing brain activity. These signals may be recorded to form the basis of an electroencephalogram (EEG).

Because conventional contact electrodes for electroencephalography must contact the scalp, any hair must be displaced. This hair displacement is generally achieved through the use of different mechanical designs. For example, a comb-like design has protrusions in a comb pattern that penetrate through the hair and make contact with the scalp when enough pressure is applied. However, this approach causes varying degrees of discomfort to the user. Furthermore, the contact gel dehydrates over time, reducing the quality of the measurements.

SUMMARY

As noted above, scalp hair can impair the function of an electroencephalography electrode. The disclosed non-contact electrodes can overcome this problem through capacitive coupling with the scalp, with the hair acting as a dielectric. But in some cases, for example where the hair is especially full or dense, the hair may impair the function of these non-contact electrodes. In such cases, a comb-like electrode design may be preferable. Some of the disclosed embodiments feature a combination of these types of electrodes.

In general, one aspect disclosed features an apparatus, comprising: a dual electrode assembly comprising: a non-contact electrode, a dry electrode having multiple contact pins, and a housing configured to enclose the dry electrode when the dry electrode is in a first position, and to expose the multiple contact pins outside the housing when the dry electrode is in a second position.

Embodiments of the system may include one or more of the following features. Some embodiments comprise an amplifier circuit having an input electrically coupled to the non-contact electrode and the dry electrode. Some embodiments comprise a capacitor electrically coupled in series between (i) the non-contact electrode and the dry electrode and (ii) the amplifier circuit. In some embodiments, a capacitance of the capacitor is approximately 10 nF. In some embodiments, the amplifier circuit comprises an amplifier powered at a supply voltage and having an input electrically coupled to the capacitor; and the input of the amplifier is biased at approximately half the supply voltage. Some embodiments comprise a connector electrically coupled to an output of the amplifier circuit.

Some embodiments comprise a head-worn device having an interior surface, wherein the dual electrode assembly is mounted upon the interior surface of the head-worn device. In some embodiments, the head-worn device is one of: a ball cap; or a helmet. In some embodiments, the head-worn device is a strap. In some embodiments, the head-worn device is one of: a virtual reality headset; or an augmented reality headset.

Some embodiments comprise a switch configured to keep the dry electrode in the first position when the switch is in a first position. Some embodiments comprise a switch configured to keep the dry electrode in the first position when the switch is in a third position. Some embodiments comprise a spring configured to urge the dry electrode toward the second position. In some embodiments, the switch is further configured to allow the dry electrode to move toward the second position when the switch is in a fourth position.

In some embodiments, the housing comprises a surface having multiple ports, wherein the contact pins of the dry electrode extend through the ports when the dry electrode is in the second position. In some embodiments, the dry electrode comprises a plate, wherein the contact pins are mounted on a first surface of the plate. Some embodiments comprise a spring (i) disposed between the housing and a second surface of the plate and (ii) configured to urge the dry electrode toward the second position. In some embodiments, the plate is a disc. In some embodiments, a diameter of the contact pins is approximately 2 mm; and a length of the contact pins is approximately 8 mm. In some embodiments, the dry electrode is coated with at least one of: gold; silver; and silver chloride.

In general, one aspect disclosed features an apparatus, comprising: a flexible electrode; an amplifier circuit having an input electrically coupled to the electrode; and a curved substrate, wherein the flexible electrode is mounted on the curved substrate.

Embodiments of the apparatus may include one or more of the following features. In some embodiments, the curved substrate has a convex surface and a concave surface; and at least a first portion of the flexible electrode is mounted on the concave surface of the curved substrate. In some embodiments, the amplifier circuit is mounted on the convex surface of the curved substrate. In some embodiments, the first portion of the flexible electrode is distal to the amplifier and is mounted on the concave surface of the curved substrate; and a second portion of the flexible electrode is proximal to the amplifier and is mounted on the convex surface of the curved substrate.

Some embodiments comprise a backing material having a concave surface, wherein the convex surface of the substrate is mounted on the concave surface of the backing material. Some embodiments comprise a head-worn device having an interior surface, wherein the backing material has a mounting surface opposite the convex surface, and wherein the mounting surface of the backing material is mounted upon the interior surface of the head-worn device.

In some embodiments, the head-worn device is one of: a ball cap; or a helmet. In some embodiments, the head-worn device is a strap. In some embodiments, the head-worn device is one of: a virtual reality headset; or an augmented reality headset.

Some embodiments comprise a capacitor electrically coupled in series between the electrode and the amplifier circuit. In some embodiments, a capacitance of the capacitor is approximately 10 nF. In some embodiments, the amplifier circuit comprises an amplifier powered at a supply voltage and having an input electrically coupled to the capacitor; and the input of the amplifier is biased at approximately half the supply voltage.

In some embodiments, the concave surface of the curved substrate has a central angle of approximately 35 degrees and an arc length of approximately 40 mm. In some embodiments, the first portion of the flexible electrode has a width of approximately 17 mm. In some embodiments, the first portion of the flexible electrode has a width of approximately 25 mm. In some embodiments, the concave surface of the curved substrate has a central angle of approximately 20 degrees and an arc length of approximately 50 mm. In some embodiments, the first portion of the flexible electrode has a width of approximately 17 mm.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 6 depicts both sides of an electrode device having a rectangular electrode with dimensions of approximately 25×40 mm according to some embodiments of the disclosed technology.

FIG. 7 depicts an electrode assembly with the electrode device of FIG. 4 mounted on a curved substrate according to some embodiments of the disclosed technologies.

FIG. 11A illustrates a mask 102 covering an electrode assembly for installation in a backing pad according to some embodiments of the disclosed technology. FIG. 11B illustrates the mask covering the electrode assembly installed in the backing pad 106 according to some embodiments of the disclosed technology.

FIG. 12 illustrates a ball cap having four electrode assemblies with backing pads secured to the interior surface of the ball cap according to some embodiments of the disclosed technology.

The figures are not exhaustive and do not limit the present disclosure to the precise form disclosed.

DETAILED DESCRIPTION

Some embodiments of the disclosed technologies solve drawbacks of conventional electroencephalography electrodes by providing non-dermal capacitive electrodes that do not require contact with the skin or scalp, thereby greatly improving the comfort of the user.

Embodiments of the disclosed technologies are described in terms of encephalography for humans. However, the disclosed technologies are not limited to encephalography or humans. For example, the disclosed technologies may be employed to obtain electrical readings from the skin at other locations of the human body, and to obtain electrical readings from animals. For example, the disclosed technologies may be employed in electrocardiology.

Brain activity causes charge movement on the human scalp surface. Through capacitive coupling this charge movement can cause charge movement on an electrode even when placed at a distance from the scalp. The disclosed technologies employ this principle for capacitive measurements.

In the disclosed embodiments, the conductive surface of the electrode may be positioned on the hair. The conductive surface of the electrode and the human body act like a parallel plate capacitor, forming capacitive coupling. The hair acts as a dielectric. The coupling capacitance forms the input of a high-impedance input stage for impedance transformation. The capacitive coupling equation is given by equation (1).

$$C = E_r E_0 A / d \qquad (1)$$

where,
A=electrode surface area;
d=distance between the electrode and the hair;
Er=dielectric constant of the hair; and
E0=vacuum permittivity.

Figure 1:
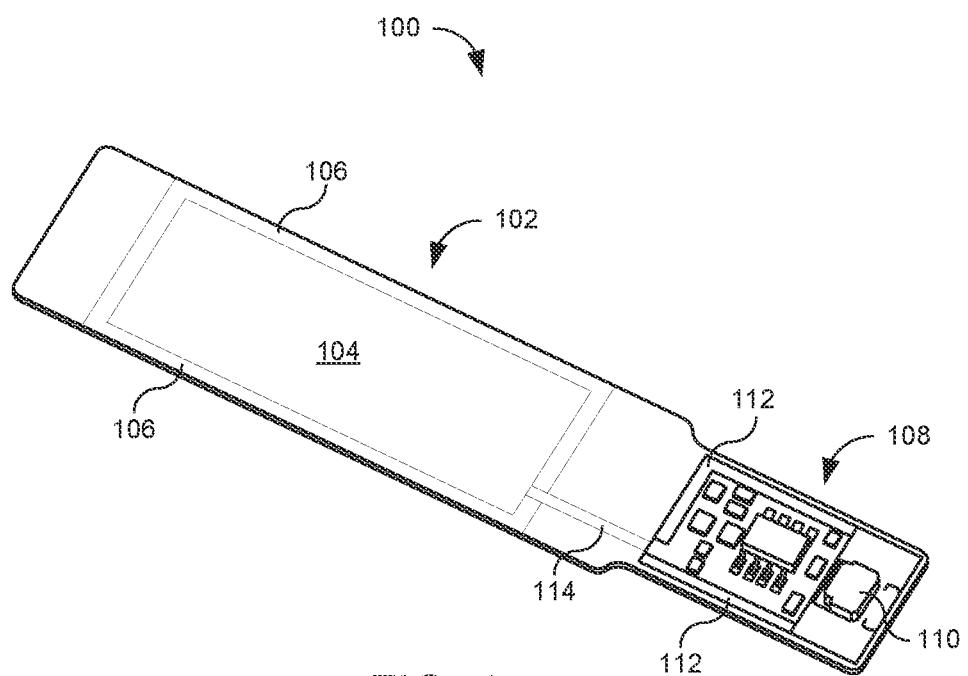
FIG. 1 illustrates a device according to some embodiments of the disclosed technologies.

FIG. 1 illustrates a device 100 according to some embodiments of the disclosed technologies. Referring to FIG. 1, the device 100 may include a flexible electrode 102 having a sensing area 104 and guard lines 106. The device 100 may also include an amplifier circuit 108 and a connector 110. The amplifier circuit 108 may be bordered by shield lines 112. The sensing area 104 may be electrically coupled to an input of the amplifier circuit 108 by a trace 114. The connector 110 may be electrically coupled to an output of the amplifier circuit 108 by a trace 114. The guard line 106 may be electrically coupled to the output of the amplifier circuit 108. The connector 110 may be connected to a device for recording and/or display. For example, the connector 110 may be connected to an EEG machine.

Figure 2:
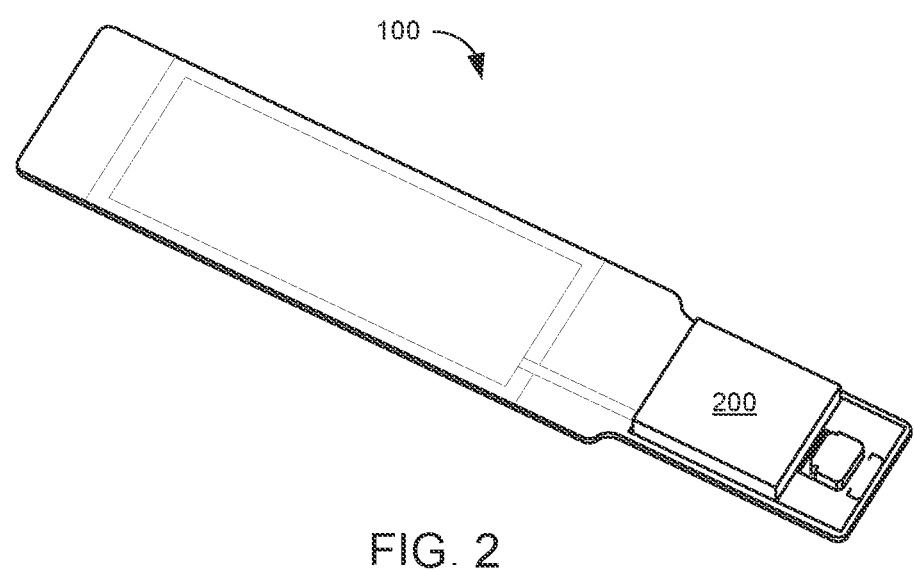
FIG. 2 illustrates the device 100 of FIG. 1 with a shield in place according to some embodiments of the disclosed technologies.

The amplifier circuit 108 may be shielded to provide protection from external noise. FIG. 2 illustrates the device 100 of FIG. 1 with a shield 200 in place according to some embodiments of the disclosed technologies. Referring to FIGS. 1 and 2, the shield 200 may be electrically coupled to the shield lines 112. The shield 200 may be made of a rigid metal. For example, the rigid metal may be rigid steel. The inside surface of the shield 200 may be insulated to avoid short circuits with components of the amplifier circuit 108.

Figure 3:
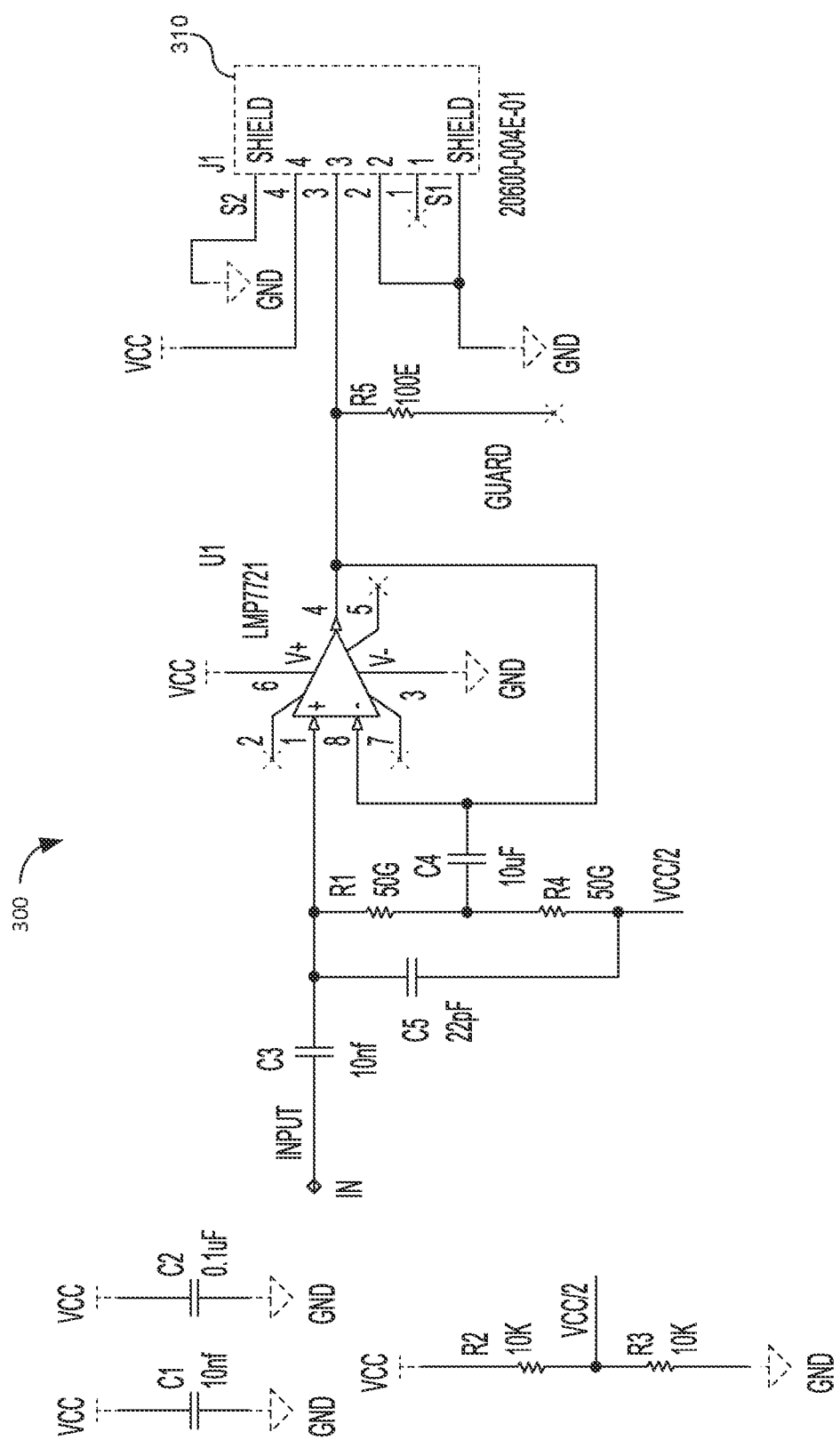
FIG. 3 is a circuit block diagram of an amplifier circuit according to some embodiments of the disclosed technology.

FIG. 3 is a circuit block diagram of an amplifier circuit 300 according to some embodiments of the disclosed technology. The amplifier circuit 300 of FIG. 3 may be used, for example, as the amplifier circuit 108 of FIG. 1. Referring to FIG. 3, the amplifier circuit 300 may be electrically coupled to a sensing area of an electrode at input IN. For example, the input IN of the amplifier circuit 300 may be electrically coupled to the sensing area 104 of the flexible electrode 102 (FIG. 1).

Referring again to FIG. 3, the amplifier circuit 300 may include an operational amplifier (OP AMP) 302. The OP AMP 302 may be implemented as differential amplifier. The differential amplifier may be implemented as a unity-gain buffer. This implementation may reduce noise and interference. The unity-gain buffer may be implemented as a very high input impedance precision amplifier with ultra-low input bias current.

The OP AMP 302 may be powered by power rails VCC and GND. The output of the OP AMP 302 may be electrically coupled to a connector 310, to the negative input of the OP AMP 302, and to the guard line via a resistor R5.

In some embodiments, amplifier circuit 300 may include an input capacitor C3 electrically coupled between the input IN and a positive input of the OP AMP 302. The input capacitor C3 may be implemented as a 10 nF capacitor. The input capacitor C3 increases the capacitance of the input IN seen by the sensing area 104 of the flexible electrode 102. The increase in impedance causes an increase in the quality of the signal obtained from the sensing area 104 of the flexible electrode 102.

In some embodiments, the signal received by the amplifier circuit 300 from the sensing area 104 of the flexible electrode 102 has both positive and negative components. In such embodiments, the positive input of the OP AMP 302 may be biased at half the supply voltage VCC. This arrangement may serve to capture all of the components of the signal received by the amplifier circuit 300 from the sensing area 104 of the flexible electrode 102.

In the embodiment of FIG. 3, the bias voltage is supplied by a bias circuit that includes capacitors C4 and C5 and a resistor divider comprising resistors R1 and R2. The bias voltage VCC/2 is provided to the positive input of the OP AMP 302 via the capacitor C5. The resistor divider is electrically coupled between the positive input of the OP AMP 302 and the bias voltage VCC/2. A center tap of the resistor divider is electrically coupled by capacitor C4 to the negative input of the OP AMP 302. Each resistor R1 and R2 may be implemented as a 50 GΩ resistor. The capacitor C4 may be implemented as a 10 uF capacitor. The capacitor C5 may be implemented as a 22 pF capacitor.

The output of the OP AMP 302 may be electrically coupled to the guard lines 106 via a resistor R5. The resistor R5 may be implemented as a 1000 resistor. In this arrangement, the guard lines 106 provide feedback that helps to avoid external noise from the environment that would otherwise contaminate the signal of interest.

Decoupling capacitors C1 and C2 may be used to decouple the power supply line from the ground and other circuits, thereby reducing the effects of noise and voltage spikes on the amplifier circuit 108. The decoupling capacitors C1 and C2 may be placed as close as feasible to the power supply filter capacitors (not shown). The capacitor C1 may be implemented as a 10 nF capacitor. The capacitor C2 may be implemented as a 0.1 uF capacitor.

In some embodiments, electrodes of certain dimensions may be used for certain positions on the head. The positions are described with reference to the international 10-20 system.

Figure 4:
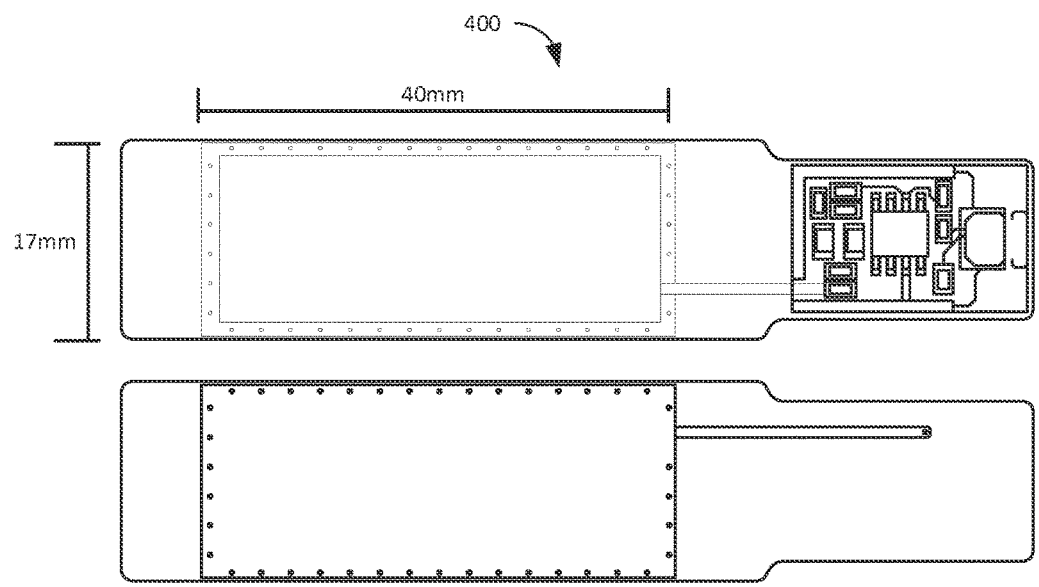
FIG. 4 depicts both sides of an electrode device having a rectangular electrode with dimensions of approximately 17×40 mm according to some embodiments of the disclosed technology.

FIG. 4 depicts both sides of an electrode device 400 having a rectangular electrode with dimensions of approximately 17×40 mm according to some embodiments of the disclosed technology. Device 400 may be used at the C3 and C4 positions of the head.

Figure 5:
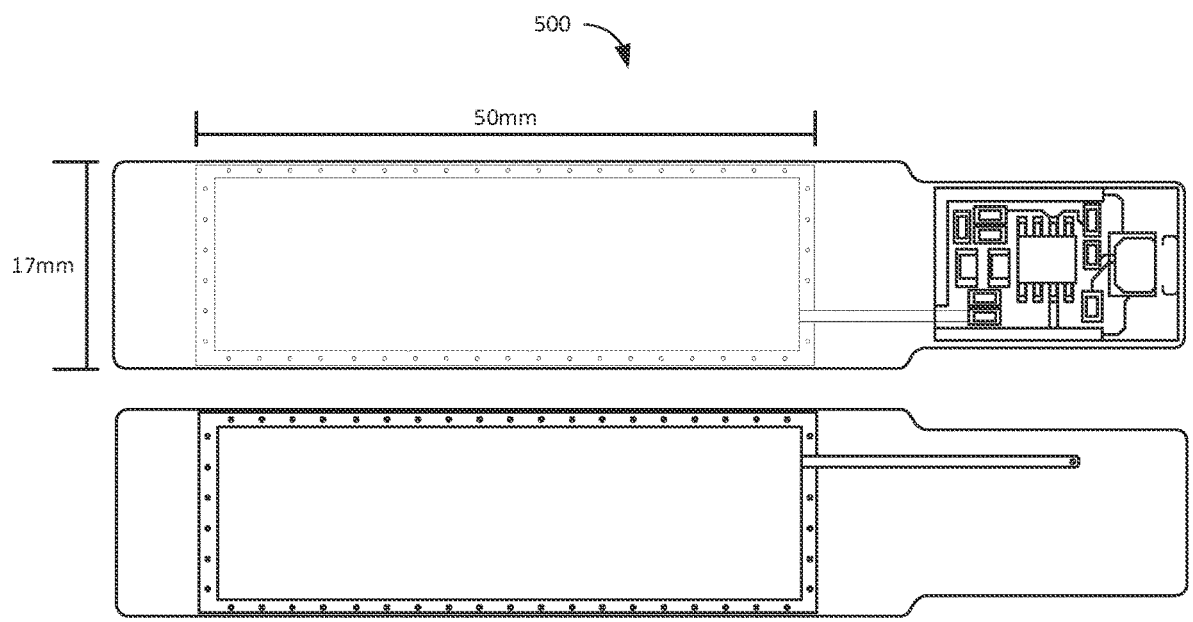
FIG. 5 depicts both sides of an electrode device having a rectangular electrode with dimensions of approximately 17×50 mm according to some embodiments of the disclosed technology.

FIG. 5 depicts both sides of an electrode device 500 having a rectangular electrode with dimensions of approximately 17×50 mm according to some embodiments of the disclosed technology. Device 500 may be used at the Fz and Cz positions of the head.

FIG. 6 depicts both sides of an electrode device 600 having a rectangular electrode with dimensions of approximately 25×40 mm according to some embodiments of the disclosed technology. Device 600 may be used at the O1 and O2 positions of the head.

In some embodiments, the flexible electrode is mounted on a curved substrate. The curved substrate may be semi-rigid. The semi-rigid substrate may be fabricated from silicone rubber, thermoplastic polyurethanes, and similar semi-rigid materials. The curved substrate may have a convex surface and a concave surface. At least a first portion of the flexible electrode may be mounted on the concave surface of the curved substrate to conform to the curvature of the head. The curvature of the electrode may increase the surface area in contact with the hair/head, resulting in an improved signal.

The curvature of the substrate may be chosen according to the desired location on the head. In some embodiments, the concave surface of the curved substrate has a central angle of approximately 35 degrees and an arc length of approximately 40 mm. Such embodiments may be used at the O1, O2, C3, and C4 positions of the head.

In some embodiments, the concave surface of the curved substrate has a central angle of approximately 20 degrees and an arc length of approximately 50 mm. Such embodiments may be used at the Fz and Cz positions of the head.

FIG. 7 depicts an electrode assembly 700 with the electrode device 400 of FIG. 4 mounted on a curved substrate 702 according to some embodiments of the disclosed technologies. The concave surface of the curved substrate 702 may have a central angle of approximately 35 degrees and an arc length of approximately 40 mm. Electrode assembly 700 may be used at the C3 and C4 positions of the head.

Figure 8:
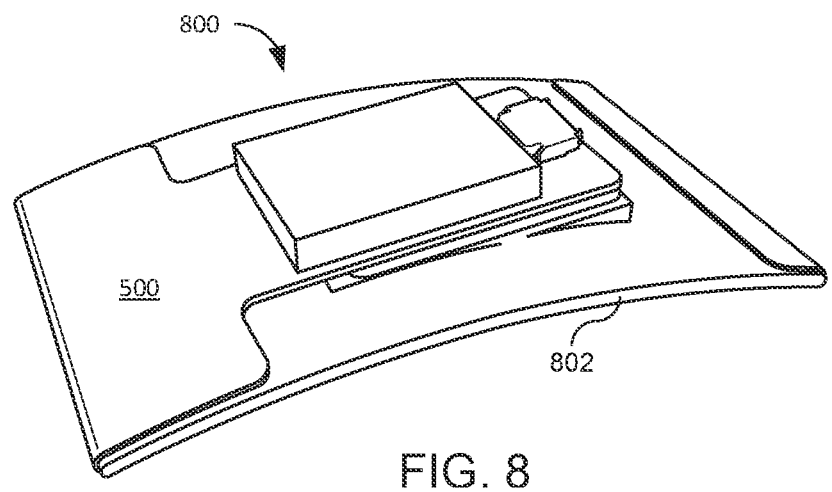
FIG. 8 depicts an electrode assembly with the electrode device of FIG. 5 mounted on a curved substrate according to some embodiments of the disclosed technologies.

FIG. 8 depicts an electrode assembly 800 with the electrode device 500 of FIG. 5 mounted on a curved substrate 802 according to some embodiments of the disclosed technologies. The concave surface of the curved substrate 802 may have a central angle of approximately 20 degrees and an arc length of approximately 50 mm. Electrode assembly 800 may be used at the Fz and Cz positions of the head.

Figure 9:
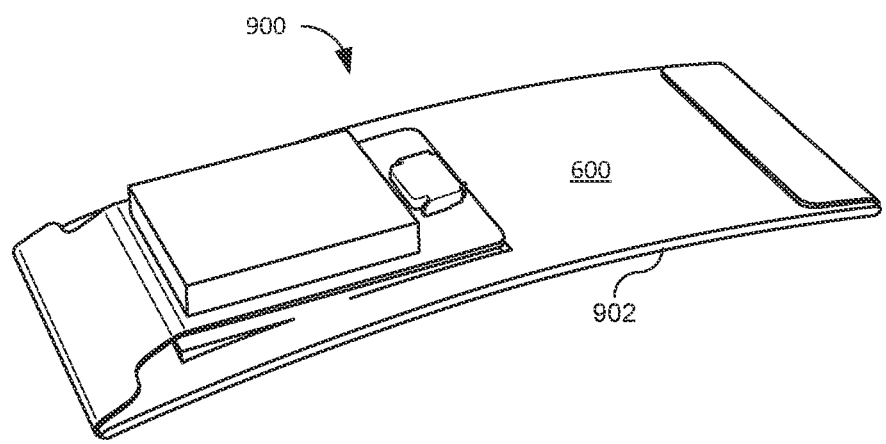
FIG. 9 depicts an electrode assembly with the electrode device of FIG. 6 mounted on a curved substrate according to some embodiments of the disclosed technologies. The concave surface of the curved substrate may have a central angle of approximately 35 degrees and an arc length of approximately 40 mm.

FIG. 9 depicts an electrode assembly 900 with the electrode device 600 of FIG. 6 mounted on a curved substrate 902 according to some embodiments of the disclosed technologies. The concave surface of the curved substrate 902 may have a central angle of approximately 35 degrees and an arc length of approximately 40 mm. Electrode assembly 900 may be used at the O1 and O2 positions of the head.

Figure 10A:
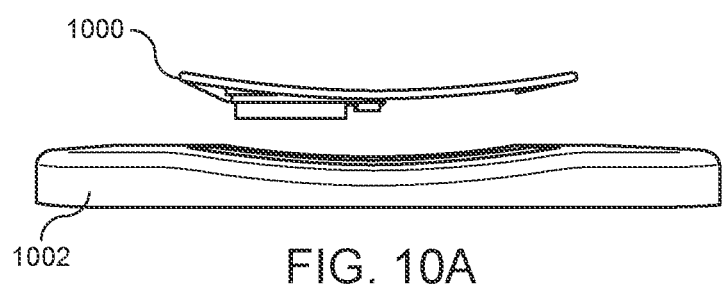
FIG. 10A illustrates an electrode assembly and a backing pad according to some embodiments of the disclosed technology.
Figure 10B:
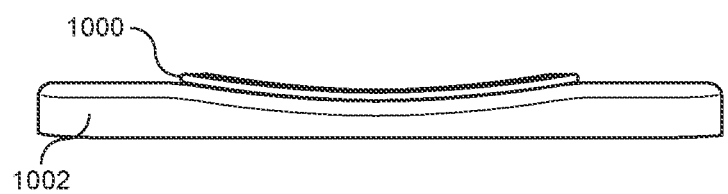
FIG. 10B illustrates the electrode assembly of FIG. 10A installed in the backing pad of FIG. 10A according to some embodiments of the disclosed technology.

The disclosed electrode assemblies may be mounted upon a backing pad for installation in a head-worn device. The backing pad may be fabricated from rubber, foam, and similar materials. The backing material may have a concave surface. The convex surface of the substrate may be mounted on the concave surface of the backing material. FIG. 10A illustrates an electrode assembly 1000 and a backing pad 1002 according to some embodiments of the disclosed technology. FIG. 10B illustrates the electrode assembly 1000 of FIG. 10A installed in the backing pad 1002 of FIG. 10A according to some embodiments of the disclosed technology.

The disclosed electrode assemblies may be secured to the disclosed backing pads by any suitable techniques. In some embodiments, a mask slightly larger than the electrode assembly may be stitched or glued to the backing pad to enclose the electrode assembly. For example, the mask may extend 2.5 mm beyond the electrode assembly on each edge. FIG. 11A illustrates a mask 1102 covering an electrode assembly 1104 for installation in a backing pad 1106 according to some embodiments of the disclosed technology. FIG. 11B illustrates the mask 1102 covering the electrode assembly 1104 installed in the backing pad 1106 according to some embodiments of the disclosed technology.

The electrode assembly with backing pad may be mounted to a head-worn device. The head-worn device may have an interior surface. The backing pad may have a mounting surface opposite its convex surface. The mounting surface of the backing pad may be mounted upon the interior surface of the head-worn device. Any mounting technique may be used. For example, the backing pad may be glued or stitched to the interior surface of the head-worn device.

Any head-worn device may be used. For example, the head-worn device may be a ball cap, a helmet, a strap, or other headwear or headgear. FIG. 12 illustrates a ball cap 1202 having four electrode assemblies with backing pads 1204A,B,C,D secured to the interior surface of the ball cap according to some embodiments of the disclosed technology. The cap 1202 may include other electrodes and/or sensors. In the example of FIG. 12, the cap 1202 includes electrodes 1206A,B,C,D, a bias electrode 1208, and a photoplethysmography (PPG) sensor 1210.

The head-worn device may have additional features. For example, the head-worn device may be a virtual reality headset or an augmented reality headset.

As noted above, scalp hair can impair the function of an electroencephalography electrode. The non-contact electrodes described above can overcome this problem through capacitive coupling with the scalp, with the hair acting as a dielectric. But in some cases, for example where the hair is especially full or dense, the hair may impair the function of these non-contact electrodes. In such cases, a comb-like electrode design may be preferable. Some embodiments feature a combination of these types of electrodes.

Figure 13A:
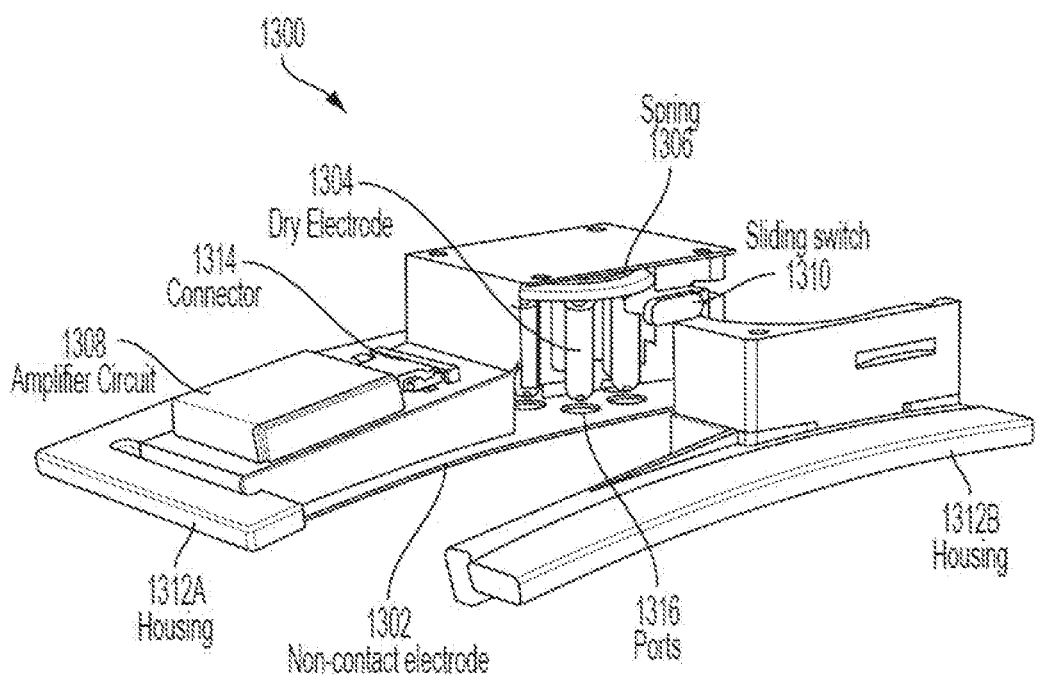
FIGS. 13A,B depict a dual electrode assembly according to some embodiments of the disclosed technologies.

FIGS. 13A,B depict a dual electrode assembly 1300 according to some embodiments of the disclosed technologies. The dual electrode assembly 1300 may include a non-contact electrode 1302 and a dry electrode 1304. The non-contact electrode 1302 may be implemented as described above.

Figure 17:
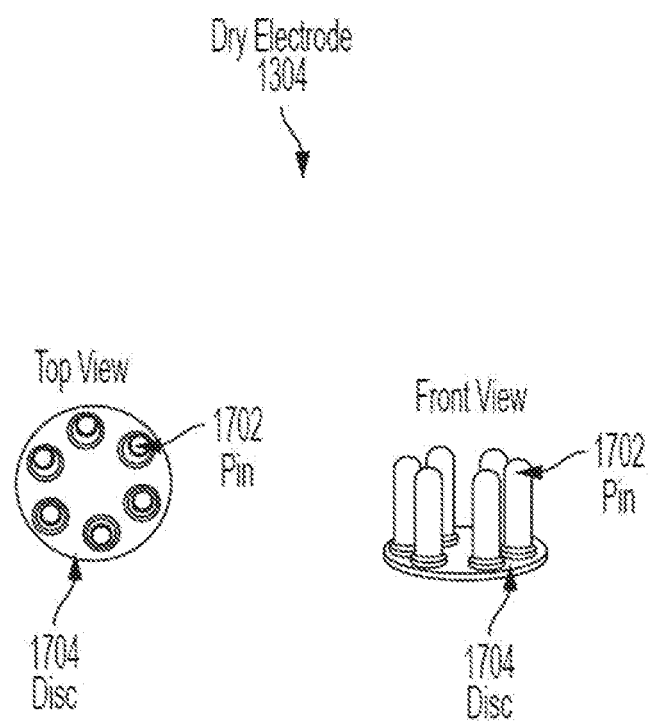
FIG. 17 illustrates the dry electrode of FIG. 13 according to some embodiments of the disclosed technology.
Figure 18:
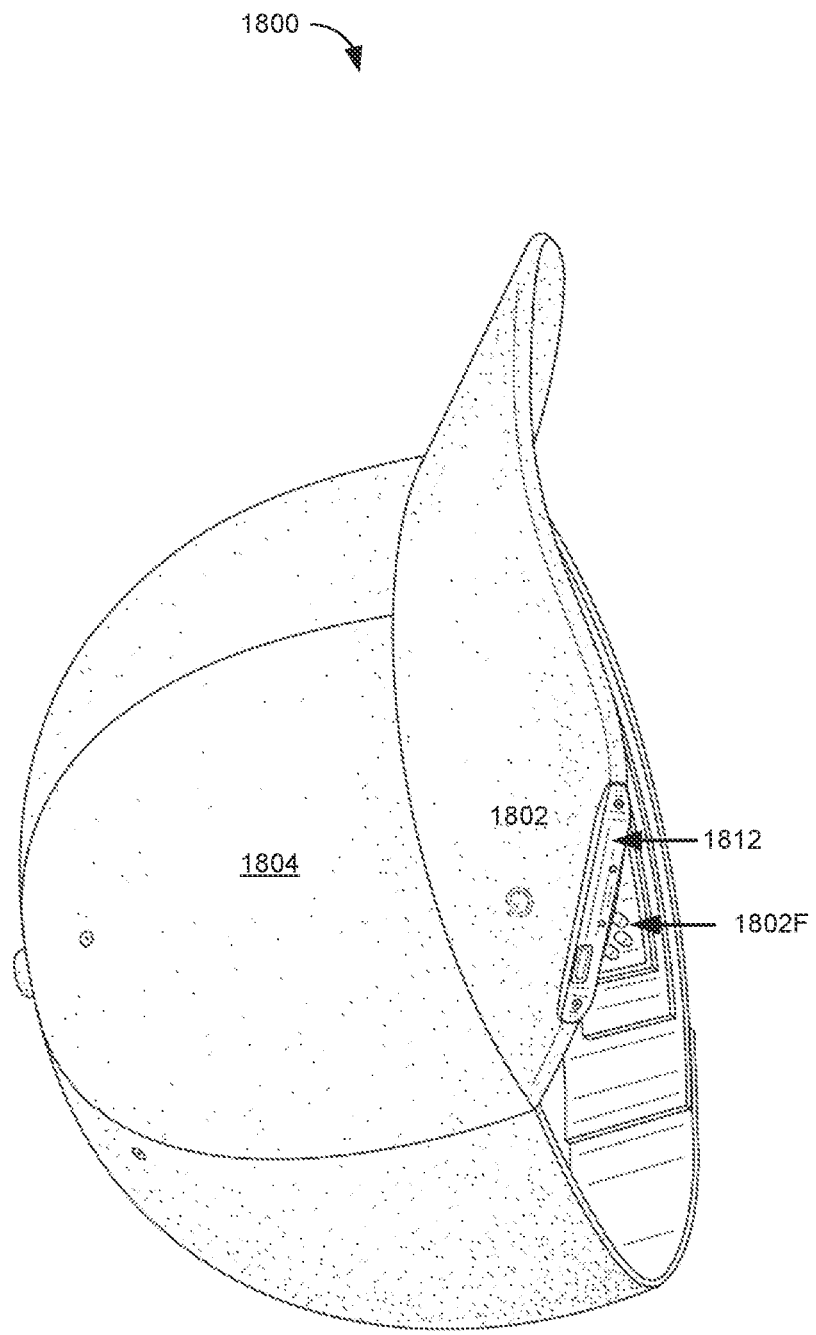
FIG. 18 is a perspective view of a new design for an electroencephalography cap.
Figure 19:
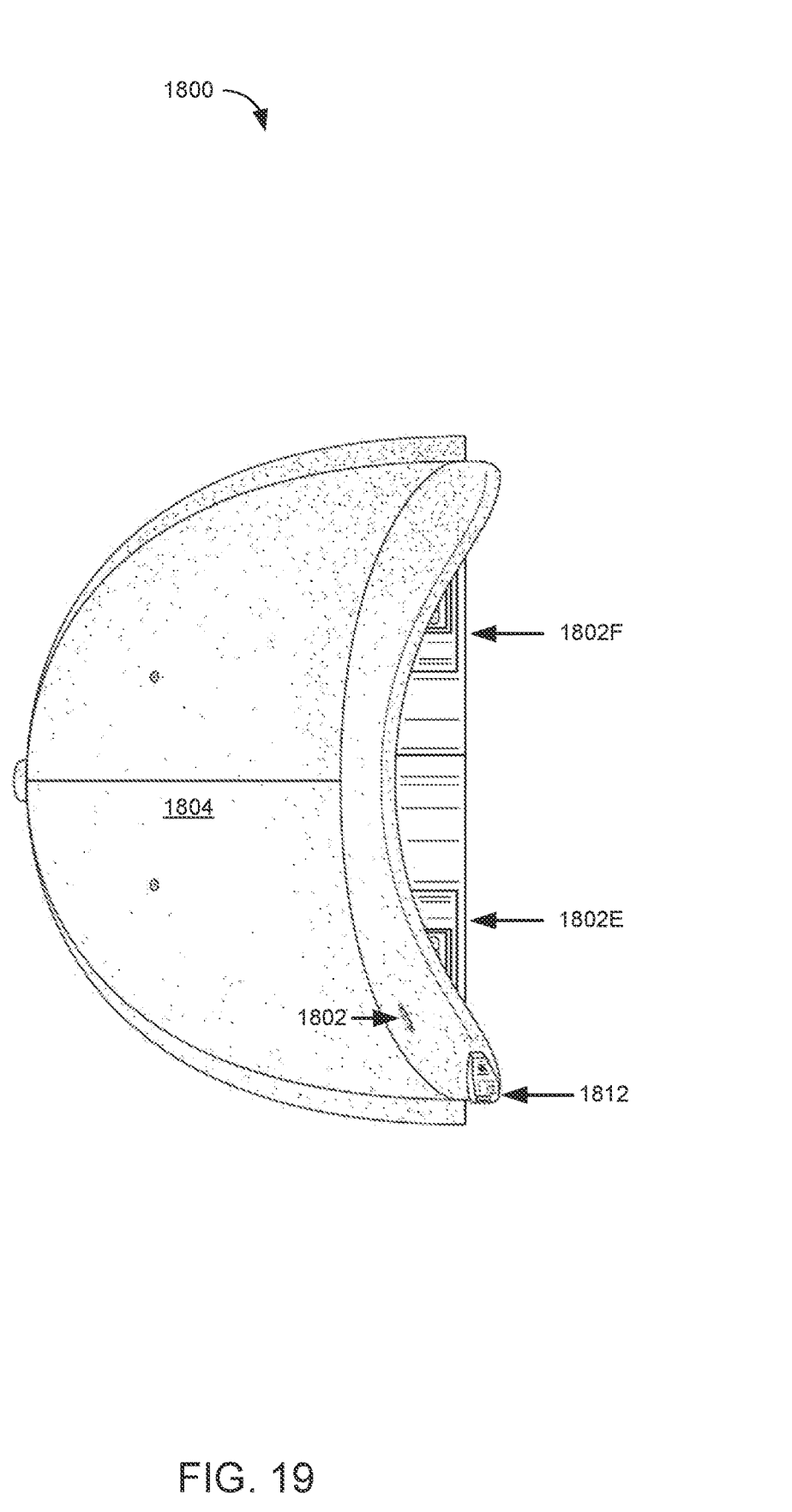
FIG. 19 is a front view of a new design for the electroencephalography cap of FIG. 18.
Figure 20:
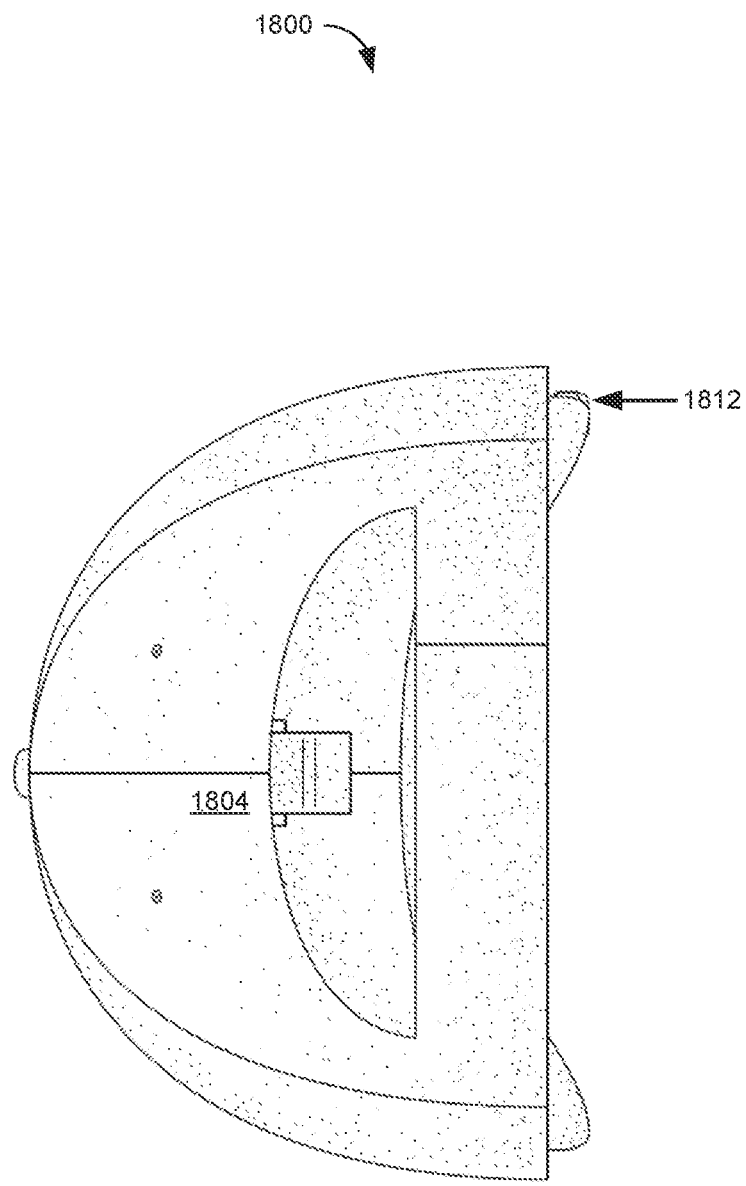
FIG. 20 is a rear view of a new design for the electroencephalography cap of FIG. 18.
Figure 21:
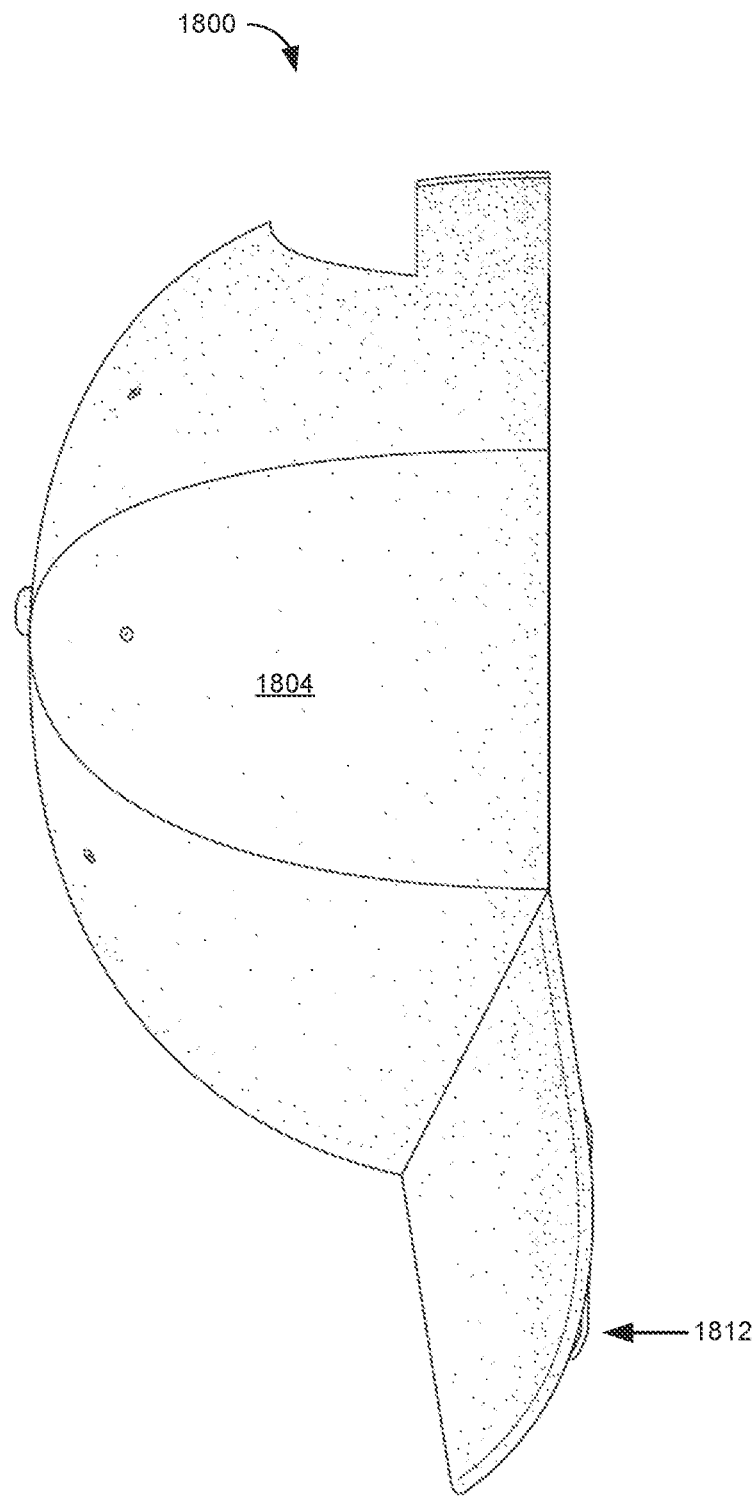
FIG. 21 is a left side view of a new design for the electroencephalography cap of FIG. 18.
Figure 22:
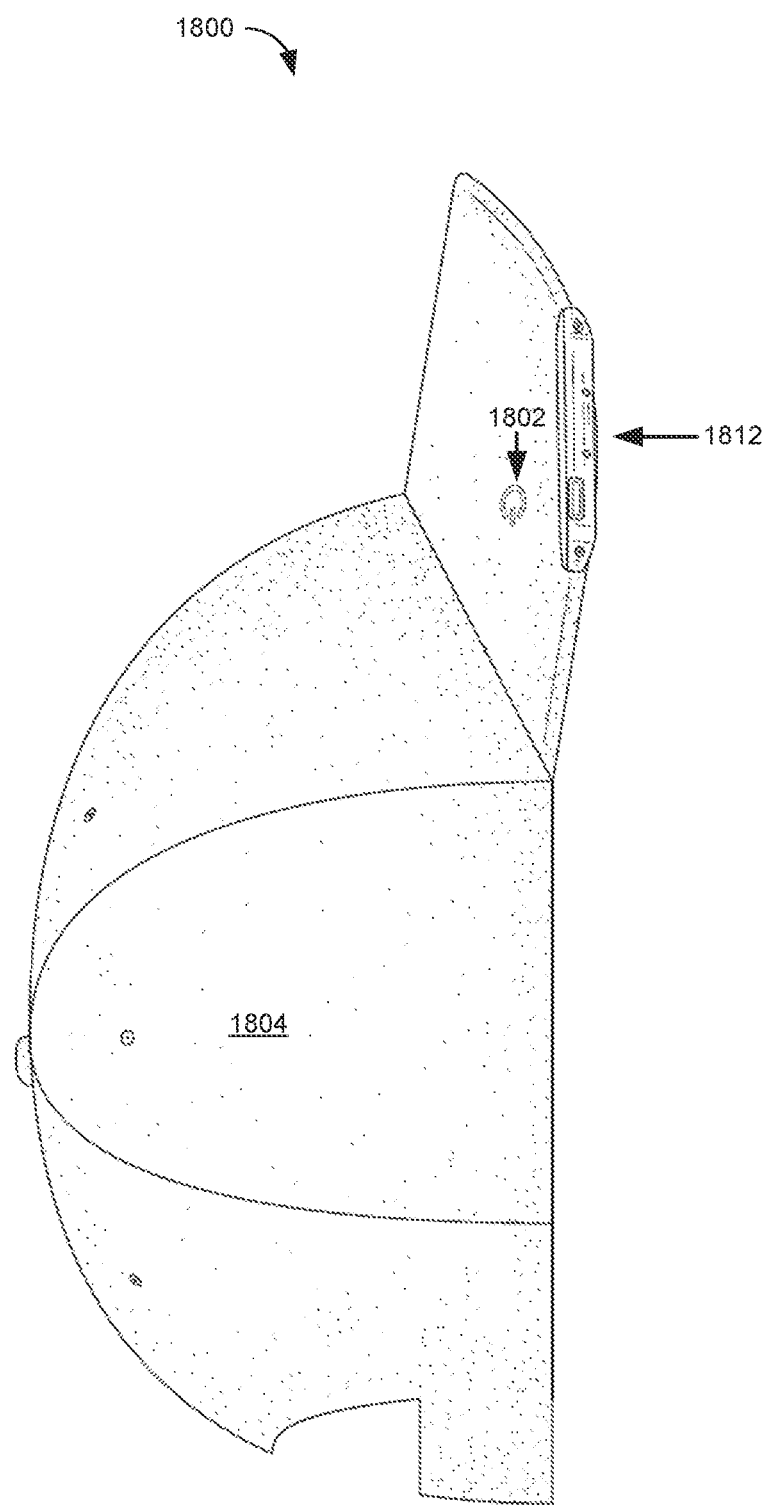
FIG. 22 is a right side view of a new design for the electroencephalography cap of FIG. 18.
Figure 23:
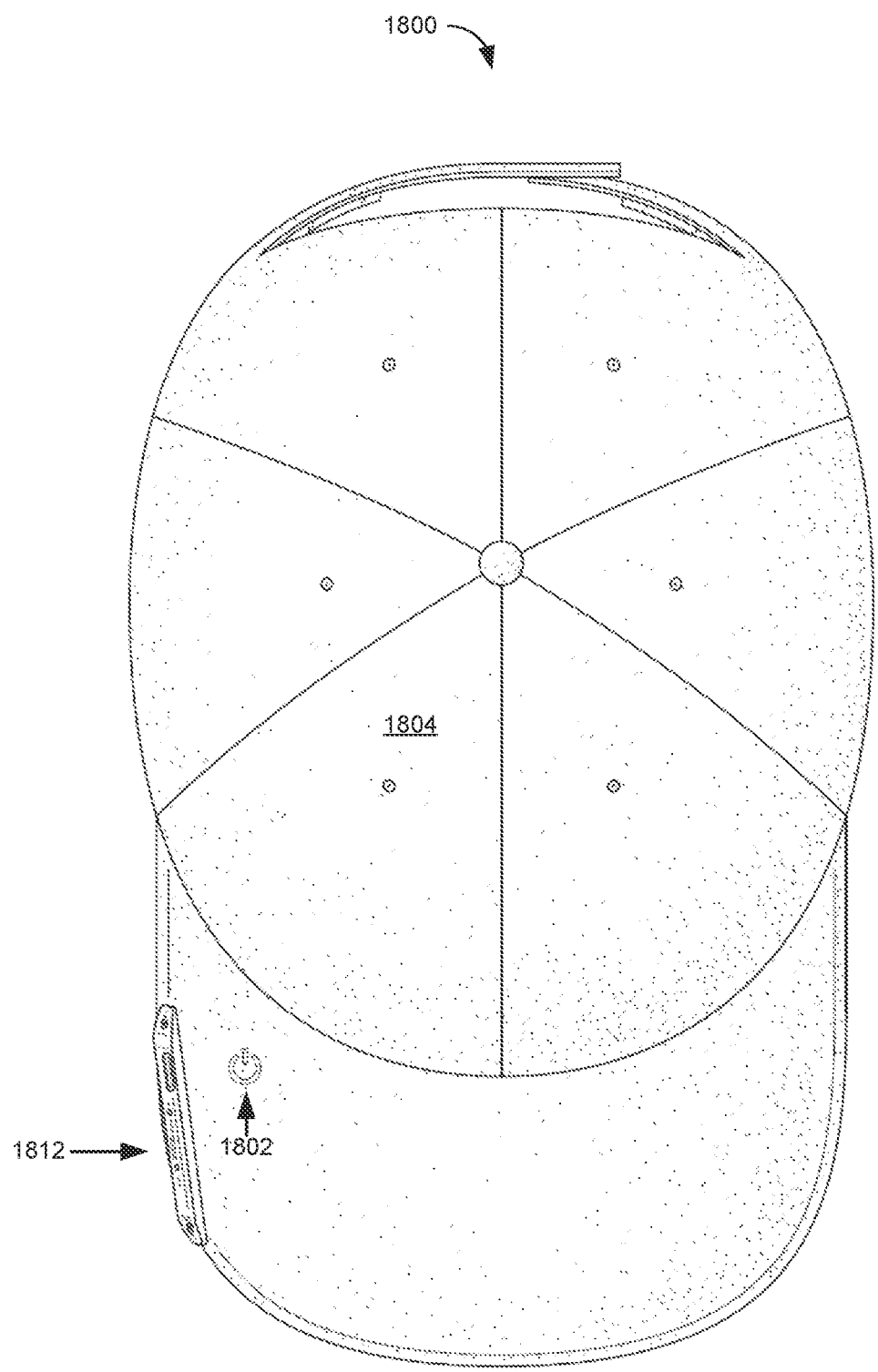
FIG. 23 is a top view of a new design for the electroencephalography cap of FIG. 18.
Figure 24:
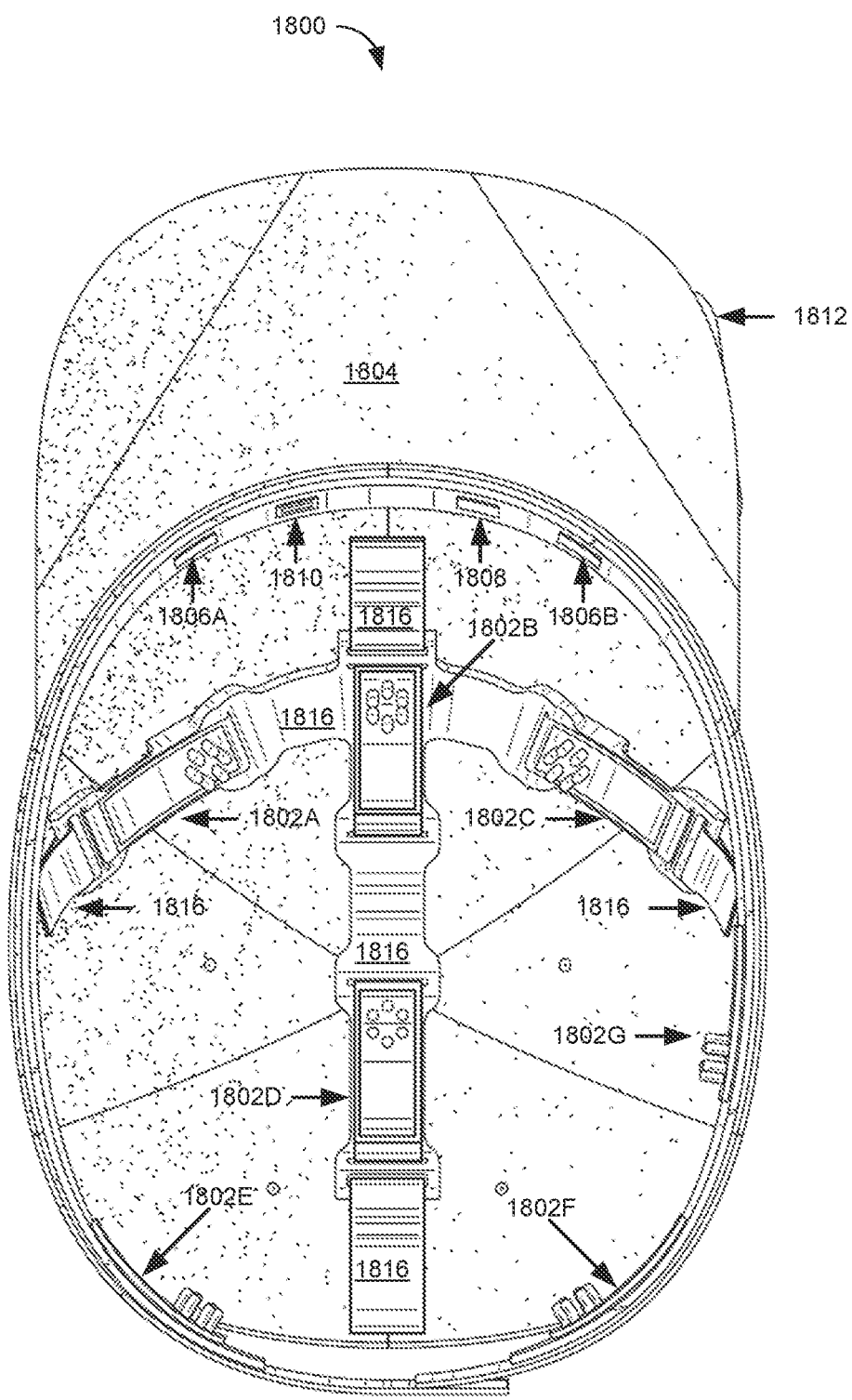
FIG. 24 is a bottom view of a new design for the electroencephalography cap of FIG. 18.

The dry electrode 1304 may have a comb design. FIG. 17 illustrates the dry electrode 1304 of FIGS. 13A,B according to some embodiments of the disclosed technology. Referring to FIG. 17, the dry electrode 1304 may include multiple contact pins 1702 extending from a plate such as disc 1704. When deployed the contact pins 1702 may contact the scalp of a patient. The dry electrode 1304 may be fabricated of brass and polymer with a coating of gold, silver, or silver chloride. The diameter of the disc 1704 may be 13.5 mm. The length and diameter of the contact pins 1702 may be chosen based on a comfort analysis on different sets of population. For example, a contact pin 1702 of the dry electrode 1304 may have a diameter of approximately 2 mm and a length of approximately 8 mm.

Figure 13B:
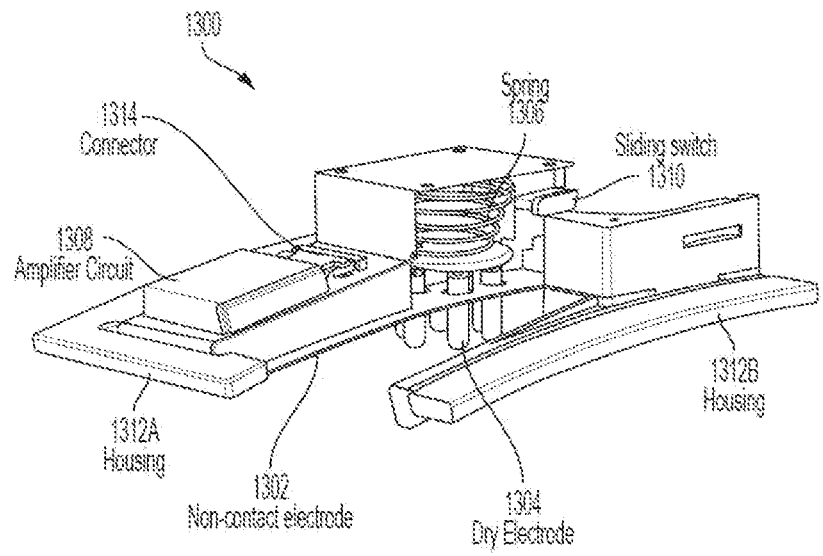

Referring again to FIG. 13A, the dry electrode 1304 may be retracted into a housing 1312A,B when not needed, and may be held in place by a sliding switch 1310 that may be manually operated by a user. When retracted, the disc 1704 of the dry electrode 1304 may compress a spring 1306. When needed, the sliding switch may be operated to release the dry electrode 1304 and decompress the spring 1306, which then deploys the pins 1702 of the dry electrode 1304 through ports 1316 in the housing 1312A,B so the pins 1702 may pass through scalp hair to contact the scalp. FIG. 13B illustrates the dual electrode assembly 1300 with the dry electrode 1304 deployed. The dry electrode 1304 may be stowed again by pressing the pins 1702 into the housing 1312A,B and returning the sliding switch 1310 to its original position.

Both electrodes 1302 and 1304 may be connected to an input of an amplifier circuit 1308. The amplifier circuit 1308 may be as described above. In some embodiments, a capacitor may be electrically coupled in series between the electrodes 1302 and 1304 and the input of the amplifier circuit 1308. A capacitance of the capacitor may be approximately 10 nF. The amplifier circuit 1308 may include an amplifier powered at a supply voltage. The input of the amplifier may be biased at approximately half the supply voltage. An output of the amplifier circuit 1308 may be connected to a connector 1314 to provide signals generated by the dual electrode assembly 1300 to other equipment.

Figure 14:
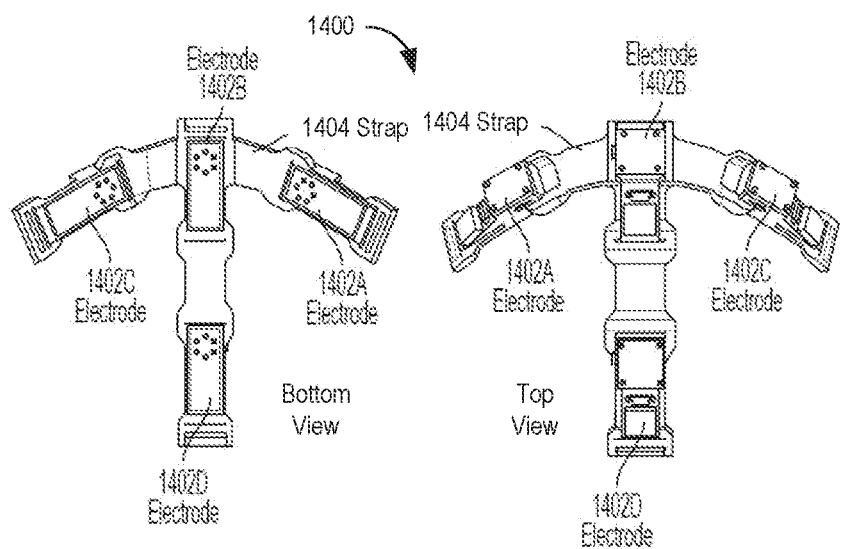
FIG. 14 depicts a headgear assembly having multiple dual electrode assemblies coupled by straps according to some embodiments of the disclosed technology.
Figure 15:
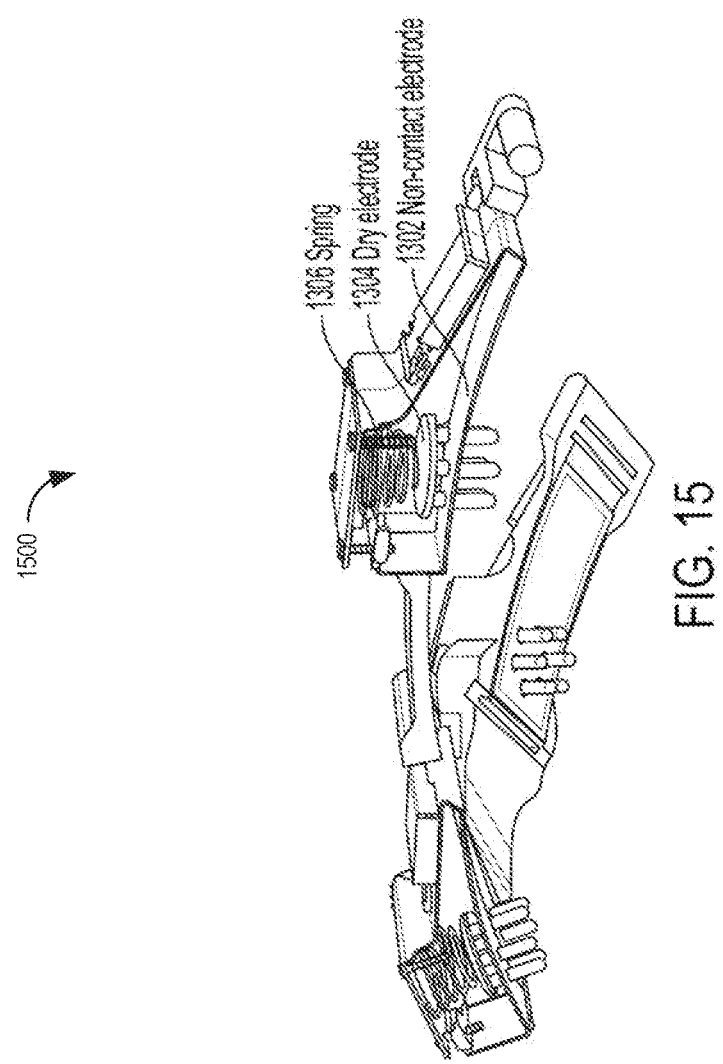
FIG. 15 depicts another headgear assembly.

FIG. 14 depicts a headgear assembly 1400 having multiple dual electrode assemblies 1402A,B,C,D coupled by straps 1404 according to some embodiments of the disclosed technology. The headgear assembly 1400 may be installed into any supporting headgear for placement on a patient's head. FIG. 15 depicts another headgear assembly 1500.

Figure 16:
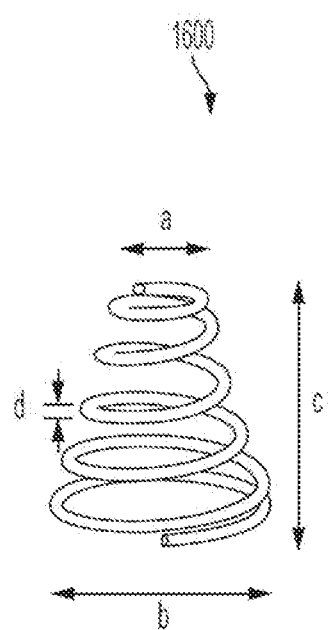
FIG. 16 depicts a spring according to some embodiments of the disclosed technology.

FIG. 16 depicts a spring 1600 according to some embodiments of the disclosed technology. The spring 1600 of FIG. 16 may be used as the spring of the dual electrode assemblies described herein. For example, the spring 1600 of FIG. 16 may be used as the spring 1306 of the dual electrode assembly 1300 of FIGS. 13A,B. The spring 1306 may have a conical shape as depicted, and may be made from brass. The spring 1600 may have a smaller outer diameter (a) of 7 mm, a larger outer diameter (b) of 11 mm, a free length (c) of 12 mm, and a wire diameter (d) of 0.4 mm. In some embodiments, the spring constant K was determined by hanging a 24 g mass from the spring. The spring was found to have an unloaded length of 12.0 mm and a loaded length of 29.45 mm for a displacement x of 8.45 mm. Applying Hooke's law K=mg/x yielded K=34.1948 N/m.

FIGS. 18-24 illustrate an electroencephalography cap 1800 according to some embodiments of the disclosed technology. The cap 1800 may include headgear 1804. The headgear 1804 may take any form. In the example of FIGS. 18-24, the headgear 1804 takes the form of a baseball cap. The cap 1800 may include seven dual electrode assemblies 1802E-G. Other embodiments may include other numbers of dual electrode assemblies 1802. The electrode assemblies 1802 may be joined to each other and to the headgear 1804 by one or more straps 1816. The cap 1800 may include additional electrodes 1806A,B, a bias electrode 1808, and a photoplethysmography (PPG) sensor 1810. The cap 1800 may include an interface module 1812 to connect the cap 1800 to external equipment. The cap 1800 may include a power button 1814 to power the cap 1800 on and off.

Multiple embodiments are disclosed. It should be understood that multiple embodiments may be combined, and one or more features of one embodiment may be combined with one or more features of one or more other embodiments.

As used herein, a circuit might be implemented utilizing any form of hardware, or a combination of hardware and software. For example, one or more processors, controllers, ASICS, PLAS, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

The foregoing description of the present disclosure has been provided for the purposes of illustration and description. It is not intended to be exhaustive or to limit the disclosure to the precise forms disclosed. The breadth and scope of the present disclosure should not be limited by any of the above-described exemplary embodiments. Many modifications and variations will be apparent to the practitioner skilled in the art. The modifications and variations include any relevant combination of the disclosed features. The embodiments were chosen and described in order to best explain the principles of the disclosure and its practical application, thereby enabling others skilled in the art to understand the disclosure for various embodiments and with various modifications that are suited to the particular use contemplated. It is intended that the scope of the disclosure be defined by the following claims and their equivalence.

What is claimed is:

1. An apparatus, comprising:
a head-worn device having an interior surface; and
a dual electrode assembly mounted upon the interior surface of the head-worn device, the dual electrode assembly comprising:
a non-contact electrode configured to capacitively couple with a body surface that uses hair as a dielectric when positioned on a user's head,
a dry electrode having multiple contact pins mounted on a first surface of a plate,
an amplifier circuit having an input electrically coupled to the non-contact electrode, the dry electrode, and
a curved substrate,
wherein the non-contact electrode is mounted on a concave surface of the curved substrate and a first portion of the non-contact electrode is distalto the amplifier and a second portion of the non-contact electrode is proximal to the amplifier and is mounted on a convex surface of the curved substrate, wherein the concave surface of the curved substrate has a central angle of 35 degrees and an arc length of 40 mm, and wherein the first portion of the non-contact electrode has a width of 17 mm,
and a housing comprising a surface having multiple ports configured to enclose the dry electrode when the dry electrode is in a first position, and to expose the multiple contact pins outside the housing, wherein the multiple contact pins extend through the multiple ports when the dry electrode is in a second position.

2. The apparatus of claim 1, wherein the head-worn device is one of:
a ball cap;
a helmet;
a strap;
a virtual reality headset; or
an augmented reality headset.

3. The apparatus of claim 1, the dual electrode assembly further comprising:
a capacitor electrically coupled in series between (i) the non-contact electrode and the dry electrode and (ii) the amplifier circuit.

4. The apparatus of claim 3, wherein:
a capacitance of the capacitor is 10 nF.

5. The apparatus of claim 3, wherein:
the amplifier circuit comprises an amplifier powered at a supply voltage and having an input electrically coupled to the capacitor and an output electrically coupled to one or more guard lines; and
the input of the amplifier is biased at half the supply voltage.

6. The apparatus of claim 3, further comprising:
a connector electrically coupled to an output of the amplifier circuit.

7. The apparatus of claim 1, the dual electrode assembly further comprising:
a switch configured to keep the dry electrode in the first position when the switch is in a third position, wherein the dry electrode is coated with at least one of gold, silver, and silver chloride, and wherein the multiple contact pins have a diameter of 2 mm and a length of 8 mm are mounted to the first surface of the plate.

8. The apparatus of claim 7, the dual electrode assembly further comprising:
a spring configured to urge the dry electrode toward the second position.

9. The apparatus of claim 7, wherein:
the switch is further configured to allow the dry electrode to move toward the second position when the switch is in a fourth position.

10. An apparatus, comprising:
a dual electrode assembly comprising:
a non-contact electrode configured to capacitively couple with a body surface that uses hair as a dielectric when positioned on a user's head,
a dry electrode having multiple contact pins,
an amplifier circuit having an input electrically coupled to the non-contact electrode, the dry electrode, and a curved substrate, wherein the non-contact electrode is mounted on a concave surface of the curved substrate and a first portion of the non-contact electrode is distal to the amplifier and a second portion of the non-contact electrode is proximal to the amplifier and is mounted on a convex surface of the curved substrate, wherein the concave surface of the curved substrate has a central angle of 35 degrees and an arc length of 40 mm, and wherein the first portion of the non-contact electrode has a width of 17 mm, and
a housing comprising a surface having multiple ports configured to enclose the dry electrode when the dry electrode is in a first position, and to expose the multiple contact pins outside the housing, wherein the multiple contact pins extend through the multiple ports when the dry electrode is in a second position.

11. The apparatus of claim 10, further comprising:
a capacitor electrically coupled in series between (i) the non-contact electrode and the dry electrode and (ii) the amplifier circuit.

12. The apparatus of claim 11, wherein:
the amplifier circuit comprises an amplifier powered at a supply voltage and having an input electrically coupled to the capacitor and an output electrically coupled to one or more guard lines; and
the input of the amplifier is biased at half the supply voltage.

13. The apparatus of claim 10, further comprising:
a connector electrically coupled to an output of the amplifier circuit.

14. The apparatus of claim 10, further comprising:
a switch configured to keep the dry electrode in the first position when the switch is in a third position, wherein the dry electrode is coated with at least one of gold, silver, and silver chloride, and wherein the multiple contact pins have a diameter of 2 mm and a length of 8 mm are mounted to the first surface of the plate.

15. The apparatus of claim 14, wherein:
the switch is further configured to allow the dry electrode to move toward the second position when the switch is in a fourth position.

16. The apparatus of claim 10, further comprising:
a spring configured to urge the dry electrode toward the second position.

17. The apparatus of claim 10, wherein:
the dry electrode comprises a plate, wherein the contact pins are mounted on a first surface of the plate.

* * * * *

UNITED STATES PATENT AND TRADEMARK OFFICE
CERTIFICATE OF CORRECTION

PATENT NO. : 12,245,861 B1
APPLICATION NO. : 18/512138
DATED : March 11, 2025
INVENTOR(S) : Dhiraj Jeyanandarajan Page 1 of 1

It is certified that error appears in the above-identified patent and that said Letters Patent is hereby corrected as shown below:

In the Claims

Column 10, Line 33, (Claim 1), change "distalto" to --distal to--;

Column 11, Line 1, (Claim 6), change "3," to --1,--.

Signed and Sealed this
Twenty-ninth Day of April, 2025

Coke Morgan Stewart
*Acting Director of the United States Patent and Trademark Office*